United States Patent [19]

Sundeen et al.

[11] Patent Number: 4,888,424
[45] Date of Patent: Dec. 19, 1989

[54] ACE-DIURETICS

[75] Inventors: Joseph E. Sundeen, Yardley, Pa.; David Floyd, Pennington; Ving G. Lee, Plainsboro, both of N.J.

[73] Assignee: E. R. Squibb & Sons, Inc., Princeton, N.J.

[21] Appl. No.: 583,902

[22] Filed: Feb. 27, 1984

[51] Int. Cl.$^4$ ........................................... C07D 403/12
[52] U.S. Cl. ................................... 544/288; 544/13; 544/244; 544/284; 546/22; 546/281; 548/413; 548/517; 548/527; 548/533
[58] Field of Search .................. 544/288, 13, 244, 284; 548/413, 533, 517, 527; 546/21, 22, 281

[56] References Cited

U.S. PATENT DOCUMENTS

| | | | |
|---|---|---|---|
| 4,217,347 | 8/1980 | Horovitz et al. | 424/246 |
| 4,316,906 | 2/1982 | Ondetti et al. | 424/274 |
| 4,431,644 | 2/1984 | Smith et al. | 544/13 |
| 4,431,645 | 2/1984 | Smith et al. | 544/13 |

FOREIGN PATENT DOCUMENTS 0088350 9/1983 European Pat. Off. .

Primary Examiner—Glennon R. Hollrah
Assistant Examiner—James H. Turnipseed
Attorney, Agent, or Firm—Donald J. Barrack

[57] ABSTRACT

Hypotensive activity is exhibited by compounds having the formulas

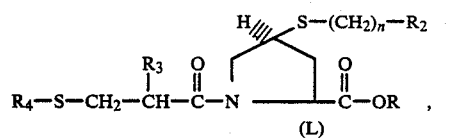

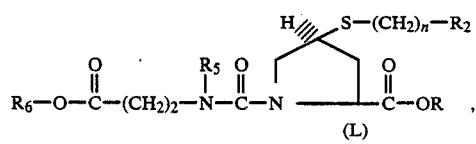

and

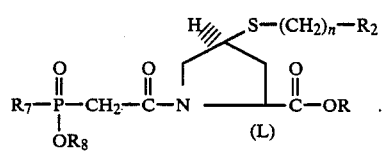

15 Claims, No Drawings

ACE-DIURETICS

BACKGROUND OF THE INVENTION

Angiotensin converting enzyme (ACE) inhibitors are known in the art to be useful hypotensive agents. Captopril, the first commercially available ACE inhibitor, is disclosed in U.S. Pat. No. 4,105,776. The prior art is replete with references describing numerous additional ACE inhibitors. Exemplary are European Patent Application No. 18,549, and U.S. Pat. Nos. 4,168,267, 4,337,201 and 4,374,829, each of which describes ACE inhibitors which contain a proline moiety.

U.S. Pat. No. 4,316,906 discloses ACE inhibitors containing a 4-mercapto substituent.

The prior art also discloses the combination of an ACE inhibitor and a diuretic for use as a hypotensive agent; see, for example, U.S. Pat. No. 4,217,347.

SUMMARY OF THE INVENTION

Compounds having the formula

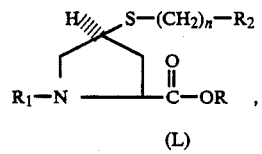

(L)

and pharmaceutically acceptable salts thereof, have hypotensive activity. In formula I, and throughout the specification, the symbols are as defined below.

R and $R_6$ are independently selected from hydrogen, alkyl, phenylmethyl and diphenylmethyl;

$R_1$ is

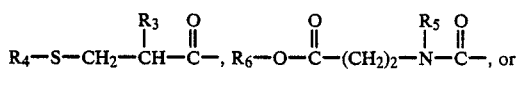

$R_2$ is

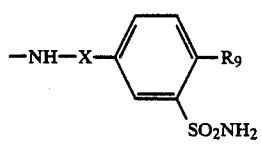

and n is 2, 3, 4 or 5, $R_2$ is

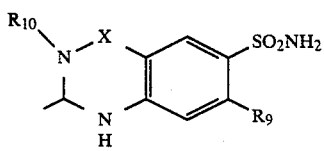

and n is 1, 2, 3 or 4, or $R_2$ is

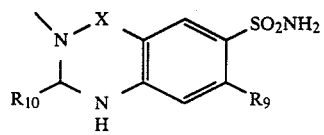

and n is 2, 3, 4 or 5, wherein X is carbonyl or sulfonyl, $R_9$ is chlorine, bromine or trifluoromethyl and $R_{10}$ is hydrogen, alkyl or aryl;

$R_3$ is hydrogen or alkyl;

$R_4$ is hydrogen or $$Y_1-\overset{O}{\underset{\|}{C}}-,$$

wherein $Y_1$ is alkyl,

$Y_2$ is hydrogen, alkyl, alkoxy, halogen or hydroxy, and m is 0, 1, 2, 3 or 4;

$R_5$ is alkyl or cycloalkyl;

$R_7$ is alkyl of 1 to 10 carbon atoms,

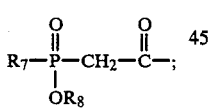

or cycloalkyl-$(CH_2)_p$-, wherein p is 0, 1, 2, 3, 4, 5, 6 or 7 and $Y_2$ is as defined above; and $R_8$ is hydrogen, alkyl, phenylmethyl, diphenylmethyl or $$-\underset{\underset{Y_3}{|}}{CH}-O-\overset{O}{\underset{\|}{C}}-Y_4,$$

wherein $Y_3$ is hydrogen, alkyl, cycloalkyl or phenyl, and $Y_4$ is hydrogen, alkyl, alkoxy, cycloalkyl, phenyl, phenylmethyl or 2-phenylethyl.

The terms "alkyl" and "alkoxy", as used throughout the specification, unless otherwise defined, refer to straight and branched-chain groups having up to seven carbon atoms.

The term "halogen", as used throughout the specification, refers to chlorine, bromine and fluorine.

The term "cycloalkyl", as used throughout the specification, refers to a cycloalkyl group having 3, 4, 5, 6 or 7 carbon atoms.

The term "aryl", as used throughout the specification, refers to phenyl and phenyl substituted with one, two or three alkyl, alkoxy and halogen atoms.

DETAILED DESCRIPTION OF THE INVENTION

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme to angiotensin II. The latter is an active pressor substance which has been implicated as the causative agent in several forms of hypertension in various mammalian species, e.g., humans. The compounds of this invention intervene in the angiotensinogen→(renin)-→angiotensin I→angiotensin II sequence by inhibiting angiotensin converting enzyme and reducing or eliminating the formation of the pressor substance angiotensin II. The compounds of formula I also possess diuretic activity. Thus, by the administration of a compositon containing one or a combination of the compounds of the invention, hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is administered orally or by parenteral routes such as the subcutaneous, intramuscular, intravenous or intraperitoneal routes.

The compounds of formull.a I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be prepared from an N-protected-4-mercaptoproline ester having the formula

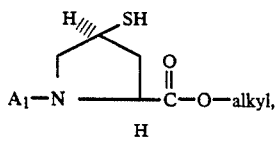

wherein $A_1$ is a nitrogen protecting group. Compounds of the above formula are described in U.S. Pat. No. 4,316,906.

To prepare a compound of formula I wherein $R_2$ is

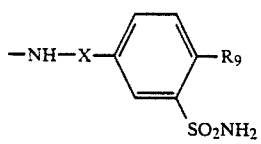

and n is 2, 3, 4 or 5, a compound of formula II is reacted with a compound having the formula

wherein $n^1$ is 2, 3, 4 or 5 and $A_2$ is a nitrogen protecting group, to obtain a compound having the formula

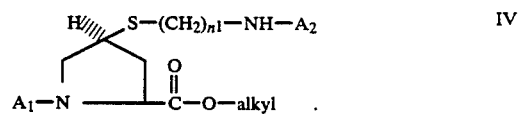

The protecting groups $A_1$ and $A_2$ should be chosen to allow for the removal of the $A_2$ protecting group without removal of the $A_1$ protecting group. Exemplary groups are the t-butyloxycarbonyl and benzyloxycarbonyl groups. The reaction of a compound of formula II with a compound of formula III proceeds in the presence of sodium iodide and a base.

Removal of the $A_2$ protecting group from a compound of formula IV yields the corresponding compound having the formula

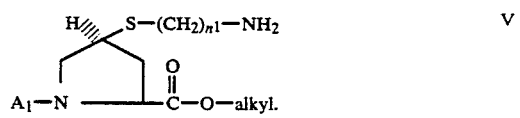

The particular deprotection reaction used will, of course, depend on the particular $A_2$ protecting group; these reactions are well known in the art.

Reaction of a compound of formula V with a compound having the formula

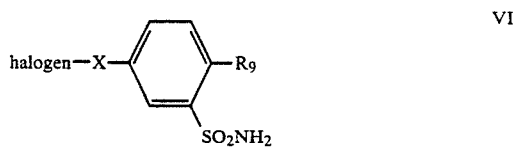

is run in the presence of a base such as triethylamine, and yields a compound having the formula

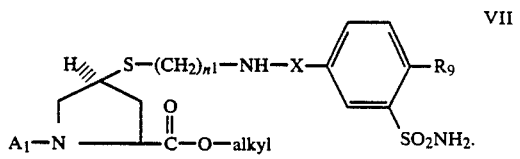

The protected compound of formula VII can be deprotected using conventional techniques and then reacted with a carboxylic acid having the formula

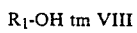

in the presence of a coupling agent such as dicyclohexylcarbodiimide or diphenylphosphoryl azide to yield a compound having the formula

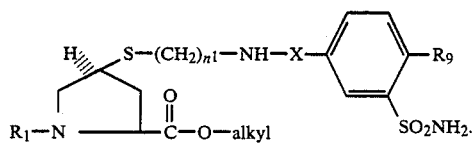 IX

Carboxylic acids of formula VIII are described in the literature; see U.S. Pat. No. 4,105,776 for a descripton of compounds of formula VIII wherein $R_1$ is

see European Patent Application No. 18,549 for a description of compounds of formula VIII wherein $R_1$ is

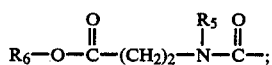

see U.S. Pat. Nos. 4,168,267 and 4,337,201 for a description of compounds of formula VIII wherein $R_1$ is

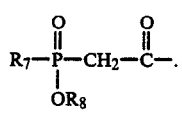

The compounds of formula IX can be hydrolyzed and, if desired, re-esterified to yield the desired compounds of formula I wherein $R_2$ is

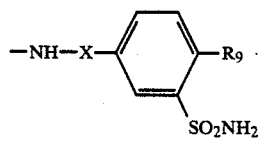

and n is 2, 3, 4 or 5.

Alternatively, the compounds of formula VII can be hydrolyzed to yield a compound having the formula

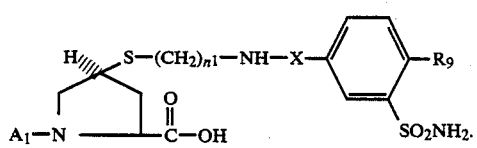 X

Deprotection of a compound of fomula X yields a compound having the formula

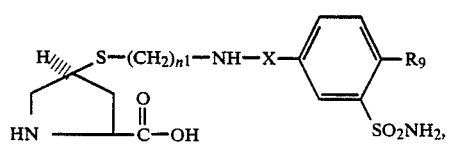 XI which can be coupled with a carboxylic acid of formula VIII to yield the desired compounds of formula I wherein $R_2$ is

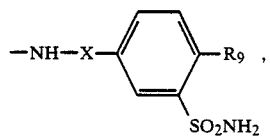

n is 2, 3, 4 or 5 and R is hydrogen. These compounds can, of course, be used to give the corresponding esters of formula I.

Still another route for preparing the compounds of this invention wherein $R_2$ is

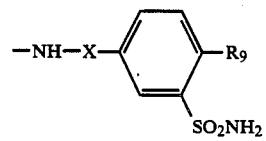

and n is 2, 3, 4 or 5 utilizes as a starting material a compound having the formula

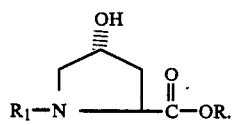 XII

After protecting any reactive groups on the $R_1$ and carboxyl side-chains, the 4-hydroxyl group can be reacted with p-toluenesulfonyl chloride in pyridine to yield a compound having the formula

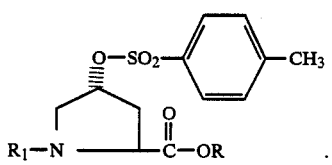 XIII

Reaction of a thiol having the formula

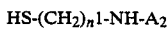 XIV with a strong base such as sodium hydride, followed by reaction with a compound of formula XIII, yields a compound having the formula

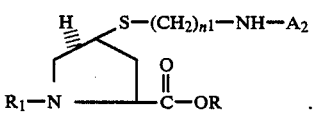 XV

Removal of the amino protecting group using conventional techniques, followed by treatment with the product of the reaction of oxalyl chloride with a compound having the formula

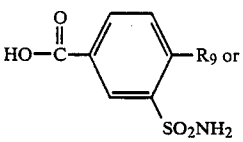 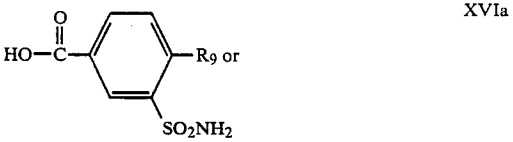 XVIa

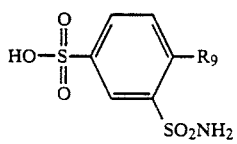

yields the corresponding compound having the formula

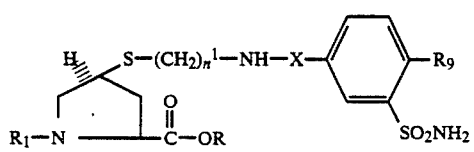
XVII

Any protecting groups present on the R₁ or carboxyl substituents can be removed to give the desired product.

Those compounds of formula I wherein R₂ is

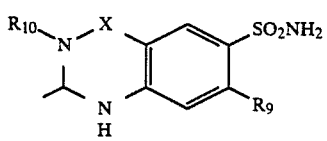

and n is 1, 2, 3 or 4 can be prepared by first reacting an N-protected-4-mercaptoproline ester of formula II with a compound having the formula halogen-$(CH_2)_{n^2}$-$CH(OY)_2$, XVIII wherein $n^2$ is 1, 2, 3 or 4 and Y is methyl or ethyl, or together the two OY groups are —O—$(CH_2)_p$—O— wherein p is 2 or 3, to yield a compound having the formula

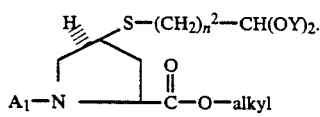
XIX

The reaction proceeds in the presence of sodium iodide and a base.

Reaction of a compound of formula XIX with a compound having the formula

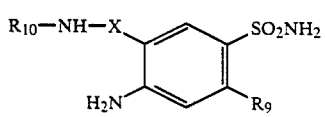
XX in the presence of p-toluenesulfonic acid yields a compound having the formula

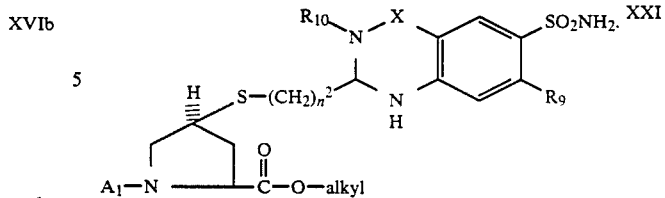
XXI

A compound of formula XXI can be converted to the corresponding product of formula I using the reaction sequences described above for the conversion of a compound of formula VII to a product of formula I.

Those compounds of formula I wherein R₂ is

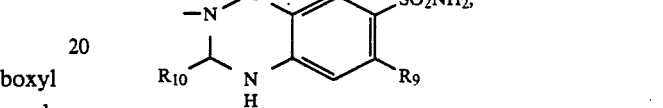

n is 2, 3, 4 or 5 and X is

can be prepared by first reacting a compound of formula V with a compound having the formula

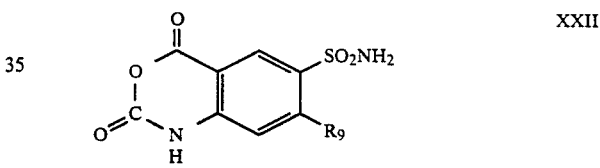
XXII in the presence of dimethylaminopyridine to yield a compound having the formula

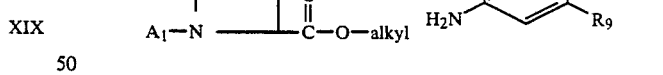
XXIII

Reaction of a compound of formula XXIII with an aldehyde having the formula

XXIV in the presence of p-toluenesulfonic acid yields the corresponding compound having the formula

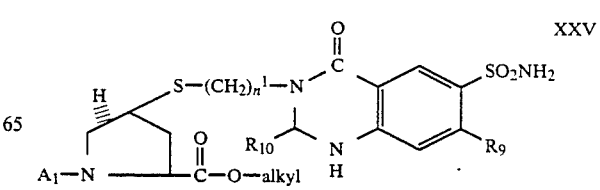
XXV

A compound of formula XXV can be converted to the corresponding product of formula I using the reacton sequences described above for the conversion of a compound of formula VII to a product of formula I.

Those compounds of formula I wherein $R_2$ is

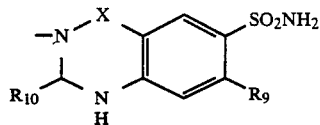

n is 2, 3, 4 or 5 and X is $SO_2$ can be prepared by first reacting a compound of formula V with a compound having the formula

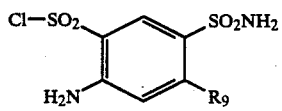   XXVI to yield a compound having the formula

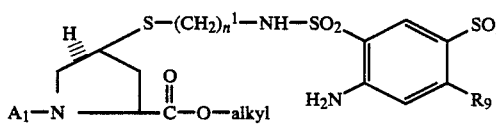   XXVII

Reaction of a compound of formula XXVII with an aldehyde of formula XXIV yields a compound having the formula

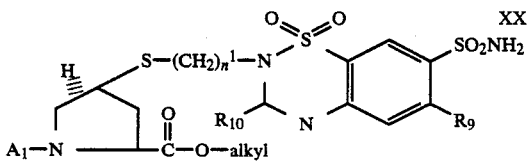   XXVIII

A compound of formula XXVIII can be converted to a product of formula I using the reaction sequences described above for the conversion of a compound of formula VII to a product of formula I.

The following examples are specific embodiments of this invention.

EXAMPLE 1

[1(S),4S]-4-[[2-[[3-(Aminosulfonyl)-4-chlorobenzoyl]amino]ethyl]thio]-1-(3-mercapto-2-methyl-1-oxopropyl-L-proline, monosodium salt (A)

[1(S),4R]-4-Hydroxy-1-[3-[[(4-methoxyphenyl)methyl]thio]-2-methyl-1-oxopropyl]-L-proline, methyl ester A solution of [1(S),4R]-1-[3-(benzoylthio)-2-methyl-1-oxopropyl]-4-hydroxyl-L-proline, diphenylmethyl ester (100 g, 19.8 mmole) dissolved in dry methanol (454 ml) was degassed under argon for 1.5 hours with stirring. Sodium methoxide (15.0 g, 0.28 mmole) was added to the solution and the reaction was stirred at room temperature overnight. Freshly prepared p-methoxybenzylchloride (43.7 g, 0.278 mole) was then added and the reaction was stirred at room temperature for 2 hours. The reaction was partitioned between ethyl acetate, diethyl ether and water. The organic layer was separated and the aqueous layer was reextracted with fresh ether (2×100 ml). The combined organic extracts were dried (magnesium sulfate), and the solvent removed under vacuum after the addition of 500 ml of silica gel. Flash chromatography (1 kg 200-60 mesh silica eluting with 30% ethyl acetate/petroether (6L) then ethyl acetate (8L)) yielded the desired product in two fractions, weighing 54.05 g and 14 g, respectively.

(B)

[1(S),4R]-4-Hydroxy-1-[3-[[(4-methoxyphenyl)methyl]thio]-2-methyl-1-oxopropyl]-4-[[(4-methylpehnyl)sulfonyl]oxy]-L-proline, methyl ester

[1(S),4R]-4-Hydroxy-1-[3-[[(4-methoxyphenyl)methyl]thio]-2-methyl-1-oxopropyl]-L-proline, methyl ester (54.05 g, 0.147 mole) was dissolved in pyridine and p-toluenesulfonyl chloride (42 g, 0.220 mole) was added over a ten minute period. The reaction mixture was stirred at room temperature, under nitrogen, for 48 hours. The reaction was poured into ice-water (2.5 L), allowed to stir for 1 hour, followed by acidifying the mixture to pH3. The solids were collected, washed with distilled water, pulverized and washed with water. After drying over phosphorous pentoxide, the compound was recrystallized from ethyl acetate: hexane (1:1), which afforded a white solid weighing 70.5 g, melting point 88°-89.5° C.

(C)

[1(S),4S]-4-[[2-[(1,1-Dimethylethoxy)carbonyl]amino]ethyl]thio]-1-[3-[[(4-methoxyphenyl)methyl]thio]-2-methyl-1-oxopropyl]-L-proline, methyl ester (2-Mercaptoethyl)carbamic acid, 1,1-dimethylethyl ester (8.85 g, 50.0 mmole) in 30 ml of dry dimethylformamide, was adcded dropwise into a stirred suspension of sodium hydride (1.08 g, 45.0 mmole) in dimethylformamide (300 ml) at room temperture. The reaction was allowed to stir at room temperature until hydrogen evolution ceased. A solution of [1(S),4R]-4-hydroxy-1-[3-[[(4-methoxyphenyl)methyl]thio]-2-methyl-1-oxopropyl]4-[[(4-methylphenyl)sulfonyl]oxy]-L-proline, methyl ester (14.85 g, 30.0 mmole) in dimethylformamide (30 ml) was added dropwise over a 10-minute period. The reaction was stirred overnight and TLC (dichloromethane:acetone (9:1)) was taken to observe the progression of the reaction. The reaction was poured into a pH4 buffer solution (300 ml) and extracted with ether:hexane (1:1), (3×250 ml). The combined organic layers were extracted with dilute bicarbonate, water, brine, and dried (sodium sulfate). The solution was evaporated under vacuum to a constant weight of 14.2 g. The product was used directly in the next step.

(D) [1(S),4S]-4-[(2-Aminoethyl)thio]-1-[3-[[(4-methoxyphenyl)methyl]thio]-2-methyl-1-oxopropyl]-L-proline, methyl ester

[1(S),4S]-4-[[2-[(1,1-Dimethylethoxy)carbonyl]amino]ethyl]thio]-1-[3-[[(4-methoxyphenyl)methyl]thio]-2-methyl-1-oxopropyl]-L-proline, methyl ester (5.5 g, 10.48 mmole) was dissolved in formic acid (100 ml, 97%) and was stirred at room temperature for 24 hours. The reaction solution was stripped of formic acid to leave a yellowish oil. This was partitioned between water (100 ml) and ethyl acetate (100 ml). Dilute sodium bicarbonate was added until the aqueous solution was at pH8. The product was extracted with ethyl acetate (4×100 ml). The organic extracts were combined, washed with water, dried (sodium sulfate), and the solvent removed in vacuo. The sample was dried to a constant weight of 3.88 g. The product was used directly in the next step.

(E)

[1(S),4S]-4-[[2-[[3-(Aminosulfonyl)-4-chlorobenzoyl-]amino]ethyl]thio]-1-[3-[[(4-methoxyphenyl)methyl]thio]-2-methyl-1-oxopropyl]-L-proline, methyl ester 3-(Aminosulfonyl)-4-chlorobenzoic acid (2.3 g, 9.78 mmole) in dichloromethane/dimethylformamide (10:1; 88 ml) was cooled to 0°–5° C. in an ice-salt bath, under argon, and oxyalyl chloride (1.45 g, 11.43 mmole) was added dropwise over a period of 5 minutes. The reaction was allowed to stir at 0° C. for 30 minutes. [1(S),4S]-4-[(2-aminoethyl)thio]-1-[3-[[(4-methoxyphenyl)methyl]thio]-2-methyl-1-oxopropyl]-L-proline, methyl ester (3.2 g, 7.5 mmole) dissolved in dichloromethane (10 ml), and triethylamine (3.68 ml, 26.4 mmole) was added dropwise over 10 minutes. The reaction was stirred at room temperture overnight, poured into ice water (200 ml), and extracted with ethyl acetate (3×150 ml). The combined organic layers were extracted with dilute aqueous hydrogen chloride (2×100 ml), water, dilute sodium bicarbonate, water, then dried (sodium sulfate), and evaported in vacuo to an oil. The desired compound was separated on a silica gel column, which was eluted with ethyl acetate:hexane (2:1), yielding 3.32 g of a white solid.

(F)

[1(S),4S]-4-[[2-[[3-(Aminosulfonyl)-4-chlorobenzoyl-]amino]ethyl]thio]-1-[3-[[(4-methoxyphenyl)methyl]thio]-2-methyl-1-oxopropyl]-L-proline

[1(S),4S]-4-[[2-[[3-(Aminosulfonyl)-4-chlorobenzoyl-]amino]ethyl]thio]-1-[3-[[(4-methoxyphenyl)methyl]thio]-2-methyl-1-oxopropyl]-L-proline, methyl ester (2.6 g, 4.04 mmole) was dissolved in tetrahydrofuran (75 ml) and methanol (20 ml). Sodium hydroxide (1N; 45 ml) was added and the resultant solution stirred at room temperature for 4 hours. The reaction was stripped of organic solvents, and the residue was dissolved in 100 ml of water followed by extraction with ethyl acetate (2×75 ml). The aqueous layer was partially evaporated to remove organic solvents and acidified to pH3. A white precipitate was observed and extracted with ethyl acetate (5×75 ml). The combined extracts were washed wtih water, dried (sodium sulfate) and the solvent removed in vacuo to yield 12.3 g of white amorphous solid, melting point 78°–81° C.

(G)

[1(S),4S]-4-[[2-[[3-(Aminosulfonyl)-4-chlorobenzoyl-]amino]ethyl]thio]-1-[2-methyl-1-oxo-3-[[(trifluoroacetyl)mercurio]thio]propyl]-L-proline

[1(S),4S]-4-[[2-[[3-(Aminosulfonyl)-4-chlorobenzoyl-]amino]ethyl]thio]-1-[3-[[(4-methoxyphenyl)methyl]thio]-2-methyl-1-oxopropyl]-L-proline (1.0 g, 1.59 mmole) in anisole (1.0 ml) and trifluoroacetic acid (10 ml) was treated with mercuric acetate (0.55 g, 1.72 mmole) at 0° C. The reaction was stirred and maintained at 0° C. for 30 minutes, after which the volume was reduced by one-half in vacuo. Diethyl ether (25 ml) was added to the solution and a white precipitate formed. The product was collected and rinsed with ether and dried to a constant weight of 1.27 g. It was used directly into the next step.

(H)

[1(S),4S]-4-[[2-[[3-(Aminosulfonyl)-4-chlorobenzoyl-]amino]ethyl]thio]-1-(3-mercapto-2-methyl-1-oxopropyl)-L-proline, monosodium salt

[1(S),4S]-4-[[2-[[3-(Aminosulfonyl)-4-chlorobenzoyl-]amino]ethyl]thio]-1-[2-methyl-1-oxo-3-[[(trifluoroacetyl)mercurio]thio]propyl]-L-proline (2.3 g, 2.85 mmole) was dissolved in acetic acid (80%) (100 ml) and hydrogen sulfide was bubbled into the solution for 30 minutes. The reaction turned from a clear solution to a black cloudy mixture. The reaction was filtered through a pad of Celite and the solvent removed in vacuo to yield 1.85 g of a yellow oil. Purification was done by generating the sodium salt with sodium bicarbonate (1.068 g, 12.7 mmole) in 30 ml of distilled water and eluting it down a gradient HP-20 column with acetonitrile:water. The desired fractions were frozen and lyophilized to a white solid, weighing 0.85 g (softens at 165° C.; melting point 170°–171° C.). Anal. Calc'd. for $C_{18}H_{23}N_3O_6S_3ClNa.2.1m\ H_2O$) (570.01) C,37.93; H, 4.81; N, 7.37; S, 16,87; Cl, 6.22. Found: C,37.93; H, 4.62; N, 7.29; S, 16.94; Cl, 6.32.

EXAMPLE 2

[1(S),4S]-4-[[2-[6-(Aminosulfonyl)-7-chloro-1,2,3,4-tetrahydro-4-oxo-2-quinazolinyl]ethyl]thio]-1-(3-mercapto-2-methyl-1-oxopropyl)-L-proline, monosodium salt (A)

[1(S),4S]-4-[[2-(1,3-Dioxolan-2-yl)ethyl]thio]-1-[3-[[(4-methoxyphenyl)methyl]thio]-2-methyl-1-oxopropyl]-L-proline, methyl ester A stirred mixture of sodium hydride (0.108 g, 4.5 mmol) in 50 ml of dry dimethylformamide was treated with 0.67 g (5.0 mmol) of 2-(2-mercaptoethyl)-1,3-dioxolane in 5 ml of dimethylformamide (dropwise addition). The reaction solution was stirred at room temperature for 1 hour and a solution of 1.485 g (3.0 mmol) of [1(S),4R]-4-hydroxy-1-[3-[[(4-methoxyphenyl)methyl]thio]-2-methyl-1-oxopropyl]-4-[[(4-methylphenyl)sulfonyl]oxy]-L-proline, methyl ester in 20 ml of dimethylformamide was added dropwise. The reaction was stirred overnight at room temperature and then poured, with stirring, into 50 ml of dilute dibasic sodium phosphate. The mixture was extracted with hexane-ether (1:1) (3×150 ml). The combined organic layers were washed sequentially with dilute sodium bicarbonate, water and finally brine. Drying over sodium sulfate and concentrating in vacuo afforded 1.22 g of the title compound.

(B)

[1(S),4S]-4-[[2-[6-(Aminosulfonyl)-7-chloro3,4-dihydro-4-oxo-2(1H)-quinazolinyl]ethyl]thio]-1-[3-[[(4-methoxyphenyl)methyl]thio]-2-methyl-1-oxopropyl]-L-proline, methyl ester To a stirred solution of 5.45 g (11.62 mmol) of [1(S),4S]-4-[[2-(1,3-dioxolan-2-yl)ethyl]thio]-1-[3-[[(4-methoxyphenyl)methyl]thio]-2-methyl-1-oxopropyl]-L-proline, methyl ester in 100 ml of acetonitrile and 2.0 ml of anisole, was added 0.3 g of p-toluenesulfonic acid. The solution was refluxed under argon for 30 minutes, cooled to 60° C., and 3.0 g (12.0 mmol) of 2-amino-5-(aminosulfonyl)-4-chlorobenzamide was added. The reaction was heated at reflux for 4 hours with axeotropic removal of water (Dean-Stark) by distillation of some of the acetonitrile. The reaction was cooled to room temperature and then partitioned between 150 ml of ethyl acetate and 100 ml of water. The aqueous layer was extracted with ethyl acetate (3×200 ml). The combined organic extracts were washed sequentially with dilute hydrochloric acid, water, and finally brine. Drying over sodium sulfate and concentrating in vacuo afforrded 5.7 g of the title compound as a yellowish oil.

(C)

[1(S),4S]-4-[[2-[6-(Aminosulfonyl)-7-chloro-3,4-dihydro-4-oxo-2(1H)-quinazolinyl]ethyl]thio]1-[3-[[4-methoxyphenyl)methyl]thio]-2-methyl-1-oxopropyl]-L-proline To a stirred solution of 1.04 g (1.55 mmol) of [1(S),-4S]-4-[[2-[6-(aminosulfonyl)-7-chloro-3,4-dihydro-4-oxo-2(1H)-quinazolinyl]ethyl]thio]'-[3-[[(4-methoxyphenyl)methyl]thio]-2-methyl-1-oxopropyl]-L-proline, methyl ester dissolved in 50 ml of tetrahydrofuran and 15 ml of methanol was added 50 ml of 1N aqueous sodium hydroxide. The reaction was stirred at room temperature for 2 hours, concentrated, and partitioned between 100 ml of ethyl acetate and 150 ml of water. The aqueous layer was extracted with ethyl acetate (3×75 ml), acidified with dilute hydrochloric acid and reextracted with ethyl acetate (3×100 ml). The combined extracts were washed with water, dried over sodium sulfate, and concentrated to yield 0.88 g of the title compound.

(D)

[1(S),4S]-4-[[2-[6-(Aminosulfonyl)-7-chloro-3,4-dihydro-4-oxo-2(1H)-quinazolinyl]ethyl]thio]-1-[2-methyl-1-oxo-3-[[(trifluoroacetyl)mercurio]thio]propyl]-L-proline A solution of 0.53 g (0.81 mmol) of [1(S), 4S]-4-[[2-[6-(aminosulfonyl)-7-chloro-3,4-dihydro-4-oxo-2(1H)-quinazolinyl]ethyl]thio]-1-[3-[[(4-methoxyphenyl)methyl]thio]-2-methyl-1-oxopropyl]-L-proline in 15 ml of trifluoroacetic acid and 1.0 ml of anisole was cooled in an ice-bath. Solid mercuric acetate (0.286 g; 0.9 mmol) was added and the reaction was allowed to stir at 0° C. for 30 minutes. The solution was diluted with 50 ml of ether and allowed to stir for an additional 10 minutes. The white precipitate was filtered and rinsed with ether. The precipitate was dried in vacuo to yield 0.67 g of the title compound.

(E)

[1(S),4S]-4-[[2-[6-(Aminosulfonyl)-7-chloro-1,2,3,4,-tetrahydro-4-oxo-2-quinazolinyl]ethyl]thio]-1-(3-mercapto-2-methyl-1-oxopropyl)-L-proline, monosodium salt To a stirred mixture of 2.22 g (2.67 mmole) of [1(S),4S]-4-[[2-[6-(aminosulfonyl)-7-chloro-3,4-dihydro-4-oxo-2(1H)-quinazolinyl]ethyl]thio]-1-[2-methyl-1-oxo-3-[[(trifluoroacetyl)mercurio]thio methyl ester in 50 ml of 80% aqueous acetic acid was treated with hydrogen sulfide gas to form the free thiol. The dark mixture was filtered through a bed of Celite and concentrated in vacuo to a dark oil. A degassed solution of 0.247 g (2.94 mmol)of sodium bicarbonate in 20 ml of distilled water was added to the oil. The resulting solution was eluted on an HP-20 column with an acetonitrile-water gradient. The desired fractions were combined and lyophilized to yield 0.586 g of the title compound as a white solid.

Analytical data calculate for $C_{19}H_{24}N_4O_6S_3Cl\cdot Na\cdot 1.55H_2O$ (586.91). C, 38.88; H, 4.65; N, 9.54; S, 16,38; Cl, 6.04; SH, 5.63. Found: C, 38.88; H, 4.63; N, 9.38; S, 16.06; Cl, 6.03; SH, 5.46.

What is claimed is:

1. A compound having the formula

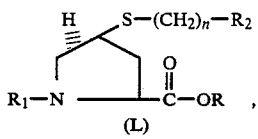

(L)

or a pharmaceutically acceptable salt thereof, wherein R and $R_6$ are each independently hydrogen, alkyl, phenylmethyl or diphenylmethyl;

$R_1$ is

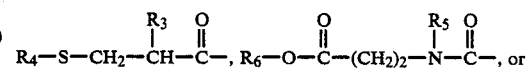

$OR_8$ $R_2$ is

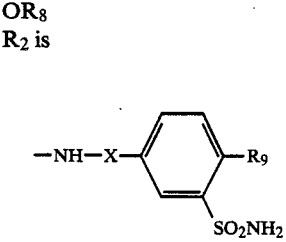

and n is 2, 3, 4 or 5, $R_2$ is

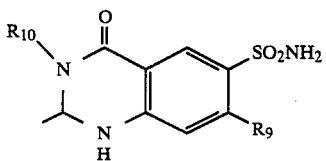

and n is 1, 2, 3 or 4, or $R_2$ is

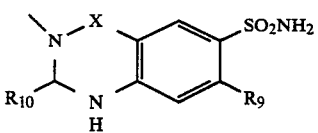

and and n is 2, 3, 4 or 5, wherein X is carbonyl or sulfonyl, $R_9$ is chlorine, bromine or trifluoromethyl and $R_{10}$ is hydrogen, alkyl or aryl;

$R_3$ is hydrogen or alkyl;

$R_4$ is hydrogen or

wherein $Y_1$ is alkyl, $$Y_2 \underset{}{\overset{}{\bigcirc}} -(CH_2)_m-, \quad \underset{S}{\overset{}{\square}} -(CH_2)_m-,$$

$$\underset{O}{\overset{}{\square}} -(CH_2)_m- \text{ or } \underset{N}{\overset{}{\bigcirc}} -(CH_2)_m-,$$

is hydrogen, alkyl, alkoxy, halogen or hydroxy, and m is 0, 1, 2, 3 or 4;

$R_5$ is alkyl or cycloalkyl;

$R_7$ is alkyl of 1 to 10 carbon atoms, $$Y_2 \underset{}{\overset{}{\bigcirc}} -(CH_2)_p-, \quad \underset{S}{\overset{}{\square}} -(CH_2)_p-,$$

$$\underset{O}{\overset{}{\square}} -(CH_2)_p-, \quad \underset{N}{\overset{}{\bigcirc}} -(CH_2)_p-$$

or cycloalkyl-$(CH_2)_p$-, wherein p is 0, 1, 2, 3, 4, 5, 6 or 7 and $Y_2$ is as defined above; and $R_8$ is hydrogen, alkyl, phenylmethyl, diphenylmethyl or $$\begin{array}{c} Y_3 \ O \\ | \ \| \\ -CH-O-C-Y_4, \end{array}$$

wherein $Y_3$ is hydrogen, alkyl, cycloalkyl or phenyl, and $Y_4$ is hydrogen, alkyl, alkoxy, cycloalkyl, phenyl, phenylmethyl or 2-phenylethyl; wherein the terms "alkyl" and "alkoxy" refer to groups having up to 7 carbon atoms; the term "cycloalkyl" refers to groups having 3, 4, 5, 6 or 7 carbon atoms; and the term "aryl" refers to phenyl and phenyl substituted with 1, 2 or 3 alkyl, alkoxy or halogen atoms.

2. A compound in accordance with claim 1 having the formula $$R_4-S-CH_2-\underset{R_3}{\overset{}{\underset{|}{C}}}H-\underset{O}{\overset{}{\underset{\|}{C}}}-N\underset{(L)}{\overset{H}{\underset{}{\bigvee}}}\overset{S-(CH_2)_n-R_2}{\underset{C-OR}{\overset{}{\underset{\|}{C}}}} ,$$

or a pharmaceutically acceptable salt thereof.

3. A compound in accordance with claim 2 wherein $R_2$ is $$-NH-\underset{O}{\overset{}{\underset{\|}{C}}}-\underset{}{\overset{}{\bigcirc}}-R_9 \atop SO_2NH_2$$

and n is 2, 3, 4 or 5.

4. A compound in accordance with claim 2 wherein $R_2$ is $$R_{10}\underset{}{\overset{O}{\underset{\|}{\underset{N}{\diagdown}}}}\underset{}{\overset{}{\bigcirc}}\overset{SO_2NH_2}{\underset{R_9}{\diagup}} \atop \underset{H}{\overset{}{\underset{N}{\diagup}}}$$

and n is 1, 2, 3 or 4.

5. A compound in accordance with claim 2 wherein $R_2$ is $$-N\underset{R_{10}}{\overset{O}{\underset{\|}{\diagdown}}}\underset{}{\overset{}{\bigcirc}}\overset{SO_2NH_2}{\underset{R_9}{\diagup}} \atop \underset{H}{\overset{}{\underset{N}{\diagup}}}$$

and n is 2, 3, 4 or 5.

6. A compound in accordance with claim 1 having the formula $$R_6-O-\underset{O}{\overset{}{\underset{\|}{C}}}-(CH_2)_2-\underset{R_5}{\overset{}{\underset{|}{N}}}-\underset{O}{\overset{}{\underset{\|}{C}}}-N\underset{(L)}{\overset{H}{\underset{}{\bigvee}}}\overset{S-(CH_2)_n-R_2}{\underset{C-OR}{\overset{}{\underset{\|}{C}}}} ,$$

or a pharmaceutically acceptable salt thereof.

7. A compound in accordance with claim 6 wherein $R_2$ is $$-NH-\underset{O}{\overset{}{\underset{\|}{C}}}-\underset{}{\overset{}{\bigcirc}}-R_9 \atop SO_2NH_2$$

and n is 2, 3, 4 or 5.

8. A compound in accordance with claim 6 wherein $R_2$ is $$R_{10}\underset{}{\overset{O}{\underset{\|}{\underset{N}{\diagdown}}}}\underset{}{\overset{}{\bigcirc}}\overset{SO_2NH_2}{\underset{R_9}{\diagup}} \atop \text{isopropyl} \underset{H}{\overset{}{\underset{N}{\diagup}}}$$

and n is 1, 2, 3 or 4.

9. A compound in accordance with claim 6 wherein $R_2$ is $R_2$ is $$-N\underset{R_{10}}{\overset{O}{\underset{\|}{\diagdown}}}\underset{}{\overset{}{\bigcirc}}\overset{SO_2NH_2}{\underset{R_9}{\diagup}} \atop \underset{H}{\overset{}{\underset{N}{\diagup}}}$$

and n is 2, 3, 4 or 5.

10. A compound in accordance with claim 1 having the formula

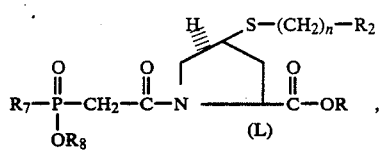

or a pharmaceutically acceptable salt thereof.

11. A compound in accordance with claim 10 wherein $R_2$ is

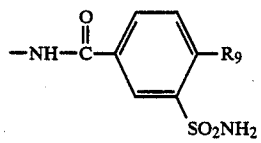

and n is 2, 3, 4 or 5.

12. A compound in accordance with claim 10 wherein $R_2$ is

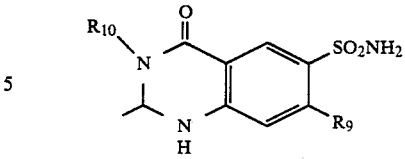

and n is 1, 2, 3 or 4.

13. A compound in accordance with claim 10 wherein $R_2$ is

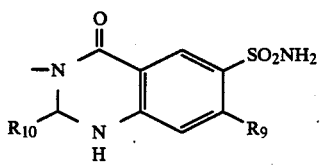

and n is 2, 3, 4 or 5.

14. The compound in accordance with claim 1, [1(S),4S]-4-[[2-[[3-(aminosulfonyl)-4-chlorobenzoyl]amino]ethyl]thio]-1-(3-mercapto-2methyl-1-oxo-propyl)-L-proline, or a pharmaceutically acceptable salt thereof.

15. The compound in accordance with claim 1, [1(S),4S]-4-[[2-[6-(aminosulfonyl)-7-chloro-1,2,3,4,-tetrahydro-4-oxo-2-quinazolinyl]ethyl]thio]-1-(3-mercapto-2-methyl-1-oxopropyl)-L-proline, or a pharmaceutically acceptable salt thereof.

* * * * *